(12) United States Patent
Zhang et al.

(10) Patent No.: US 8,803,911 B2
(45) Date of Patent: Aug. 12, 2014

(54) USER INTERFACE AND VIEWING WORKFLOW FOR MAMMOGRAPHY WORKSTATION

(75) Inventors: Heidi Daoxian Zhang, Los Gatos, CA (US); Patrick B. Heffernan, Los Gatos, CA (US); László K Tabár, Cave Creek, AZ (US)

(73) Assignee: Three Palm Software, Carmel, CA (US)

( * ) Notice: Subject to any disclaimer, the term of this patent is extended or adjusted under 35 U.S.C. 154(b) by 1100 days.

(21) Appl. No.: 12/237,290

(22) Filed: Sep. 24, 2008

(65) Prior Publication Data

US 2009/0185732 A1 Jul. 23, 2009

Related U.S. Application Data

(60) Provisional application No. 61/003,309, filed on Nov. 16, 2007.

(51) Int. Cl.
*G09G 5/14* (2006.01)
*G09G 5/377* (2006.01)
*G06T 11/60* (2006.01)

(52) U.S. Cl.
CPC ..................................... *G06T 11/60* (2013.01)
USPC ........... 345/629; 345/619; 345/419; 345/440; 345/661

(58) Field of Classification Search
CPC ....................................................... G06T 11/60
USPC .................. 345/629, 619, 419, 592, 440, 661
See application file for complete search history.

(56) References Cited

U.S. PATENT DOCUMENTS

| | | | | |
|---|---|---|---|---|
| 4,907,156 A | * | 3/1990 | Doi et al. ....................... | 382/130 |
| 5,133,020 A | * | 7/1992 | Giger et al. .................... | 382/128 |
| 5,984,870 A | * | 11/1999 | Giger et al. .................... | 600/443 |
| 5,987,345 A | * | 11/1999 | Engelmann et al. .......... | 600/407 |
| 6,058,221 A | * | 5/2000 | Bukal et al. ................... | 382/286 |
| 6,058,322 A | * | 5/2000 | Nishikawa et al. ........... | 600/408 |
| 6,492,073 B1 | * | 12/2002 | Lin et al. ........................... | 430/5 |
| 6,630,937 B2 | | 10/2003 | Kallergi et al. | |
| 6,734,880 B2 | * | 5/2004 | Chang et al. ................... | 715/738 |
| 6,925,200 B2 | * | 8/2005 | Wood et al. .................... | 382/132 |
| 6,970,587 B1 | * | 11/2005 | Rogers ............................ | 382/132 |
| 7,593,561 B2 | * | 9/2009 | Zhang et al. ................... | 382/130 |

(Continued)

OTHER PUBLICATIONS

H. Neiber et al., Local Contrast Enhancement for the Detection of Microcalcifications, Proc. 5th Intl. [ Worhso DE._DE._~tal Mammography, pp. 598-604, 2000.*

(Continued)

*Primary Examiner* — Javid A Amini
(74) *Attorney, Agent, or Firm* — Haynes and Boone, LLP

(57) ABSTRACT

This invention provides a simple user interface and sequencing viewing method for a mammography interpretation workstation. In particular, the invention includes the method and apparatus that moves the source images and the associated data using two-level of pre-fetching and caching mechanism, sequences the reading workflow (including worklist, hanging protocol, viewing sequencing), draws markup using electronic grease pan, and automatically generates the recall forms and screening reports. The user interface operates on single button and mouse wheel style to maximize the radiologists' efficiency.

15 Claims, 12 Drawing Sheets

(56) References Cited

U.S. PATENT DOCUMENTS

| | | | |
|---|---|---|---|
| 7,945,083 B2* | 5/2011 | Zhang et al. | 382/132 |
| 2004/0024292 A1* | 2/2004 | Menhardt et al. | 600/300 |
| 2004/0122790 A1* | 6/2004 | Walker et al. | 707/1 |
| 2004/0247166 A1* | 12/2004 | Giger et al. | 382/128 |
| 2006/0109526 A1* | 5/2006 | Zhang et al. | 358/487 |
| 2006/0110022 A1* | 5/2006 | Zhang et al. | 382/132 |
| 2006/0147101 A1* | 7/2006 | Zhang et al. | 382/131 |
| 2007/0274585 A1* | 11/2007 | Zhang et al. | 382/132 |
| 2007/0286466 A1* | 12/2007 | Heffernan et al. | 382/128 |
| 2008/0153012 A1* | 6/2008 | Liu et al. | 430/5 |
| 2008/0255849 A9* | 10/2008 | Gustafson | 704/275 |
| 2008/0267470 A1* | 10/2008 | Zhang et al. | 382/128 |
| 2008/0285825 A1* | 11/2008 | Zhang et al. | 382/128 |
| 2009/0171871 A1* | 7/2009 | Zhang et al. | 706/12 |
| 2009/0220138 A1* | 9/2009 | Zhang et al. | 382/132 |
| 2009/0238422 A1* | 9/2009 | Zhang et al. | 382/128 |
| 2011/0222752 A1* | 9/2011 | Zhang et al. | 382/132 |

OTHER PUBLICATIONS

Snoeren, "Thickness Correction of Mammographic Images by Means of a Global Parameter Model of the Compressed Breast", IEEE Transactions on Medical Imaging, vol. 23, No. 7, Jul. 2004.*

Disease Specific Intelligent Pre-fetch and Hanging Protocol for Diagnostic Neuroradiology Workstations; Craig A. Morioka, PhD Daniel J. Valentino, PhD Gary Duckwiler, MD Suzie El-Saden, MD Usha Sinha, PhD Alex Bui, PhD Hooshang Kangarloo, MD, 2001.*

Robert A. Schmidt, "Digital Mammography, Networking, PACS, and Dante's Inferno", Applied Radiology, Supplement to Sep. 2006, pp. 21-25.

Gillian M. Newstead, "Digital Mammography: Cost and Workflow Issues", Applied Radiology, Supplement to Sep. 2006, pp. 17-20.

Eric A. Berns et al., "Digital and Screen-Film Mammography: Comparison of Image Acquisition and Interpretation Times" AJR Women's Imaging, 187 Jul. 2006, pp. 38-41.

* cited by examiner

Exemplary Viewing Mask 700a

Exemplary Viewing Mask 700b

Exemplary Viewing Mask 700c

Exemplary Viewing Mask 700d

Exemplary Report 1000

USER INTERFACE AND VIEWING WORKFLOW FOR MAMMOGRAPHY WORKSTATION

BACKGROUND

The present invention relates generally to the field of medical imaging systems. Particularly, the present invention relates to a method and apparatus for a soft-copy reading mammography interpretation workstation.

Digital mammography images are very data-intensive. A standard 4-view study acquired on a digital system with a 50 μm detector can contain more than 140 MB of data. Even when displaying such mammographic images on two 5 megapixel monitors, the radiologist is really seeing only 7% of the information. One of the issues that radiologists face is that many of the tools that they use, such as interpretation workstations, are relatively primitive when it comes to dealing with such large amounts of data.

Screening mammography reading requires high throughput due to the large volume of screen mammograms and the low reimbursement rate. Historically, screening mammograms on film tend to performed by reading batches with the average interpretation time per case being around 1 minute including time for dictation. However the median film reading time may be as short as 15 seconds because the vast majority of screening cases are negative.

A number of studies have shown that radiologists take a significantly longer time for interpretation when reading digital mammography cases as compared to the time for screen-film mammography. Reasons for this increase in reading time include the poor performance of data transactions and inappropriate viewing workflows for mammography. These needs are not well-addressed in current picture archiving and communication system (PACS) workstations.

SUMMARY

Consistent with some embodiments, a mammography workstation is provided. The workstation may comprise at least one computer display; a computer processor connected to the at least one computer display. The computer processor may also be connected to a local memory storage device and a Digital Imaging and Communications in Medicine (DICOM) service. The workstation may also include a workstation application running on the computer processor, the workstation application may be configured to provide a user interface, the user interface may include a visualization sequencing configuration interface that includes a plurality of selectable buttons the selection of which results in a stepped visualization sequence of mammogram images. Additionally, the workstation may include at least one input device suitable to allow a user to select desired buttons of the plurality of selectable buttons and to allow a user to step through the stepped visualization sequence of medical images.

Consistent with some embodiments, a method for scrollably viewing full resolution mammogram images that have more pixels than a viewing screen used to view the images is provided. The method may include displaying a scaled image in a background of a window on a computer display, the scaled image being a full resolution mammogram image that has been scaled to fit within the window and partitioning the full resolution mammogram image into a plurality of full resolution portions, the size of the full resolution portions being determined by a user-selectable pixel area, and determining a viewing path. The viewing path may include a sequential ordering of the full resolution portions. The method may further include displaying a first full resolution portion in a full resolution frame in a foreground of the window and displaying a second full resolution portion in the full resolution frame after the first full resolution portion is displayed and when requested by a user. The second full resolution portion may be the next full resolution portion according to the sequential ordering.

DETAILED DESCRIPTION

Embodiments may provide a simple user interface and sequencing viewing method for a mammography interpretation workstation. In particular, the embodiments may include methods and systems that move the source images and the associated data using two levels of pre-fetching and caching mechanisms, sequences the reading workflow (including a worklist, hanging protocols, viewing sequencing), permit a user to draw markups using an electronic grease pen, and automatically generates recall forms and diagnosis reports. The user interface may operate on single button or a mouse wheel style to maximize the user's efficiency.

Figure 1:
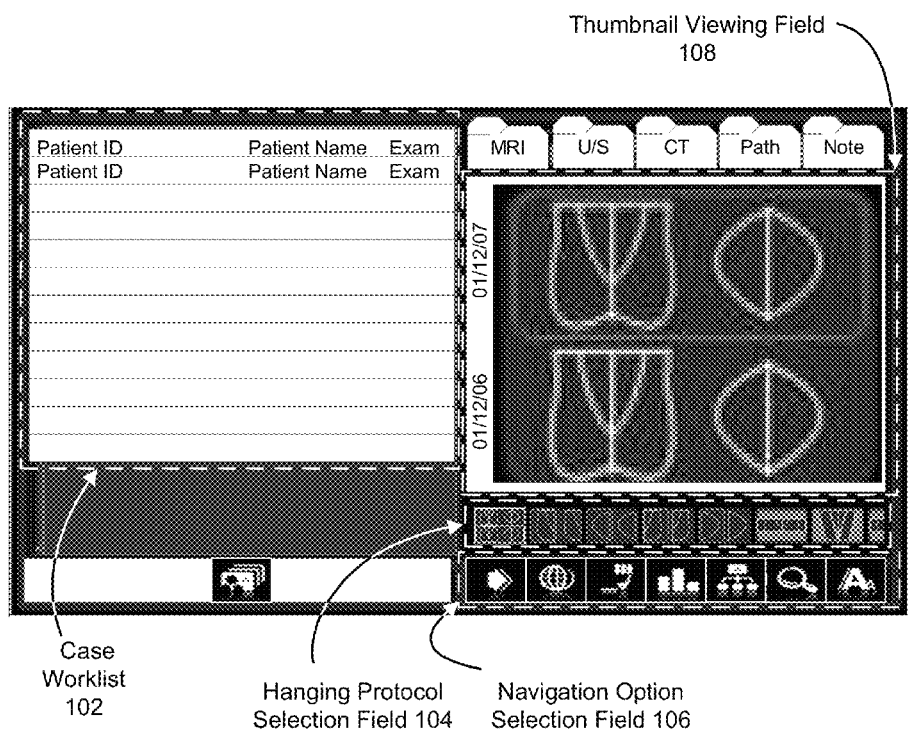
FIG. 1 depicts a navigation interface provided by a workstation.

FIG. 1 depicts a navigation interface provided by a mammography workstation. The workstation consists of two display screens or interfaces: a navigation interface 100 and an image interface. Although the two screens or interfaces may physically reside on a single monitor; the two screens may physically reside on two or more monitors. The navigation interface 100 may be used for navigating patient/exam lists such as case worklist 102, for navigating hanging protocols in a hanging protocol selection field 104; or for navigating viewing protocol in navigation option selection field 106. Navigation interface 100 may also provide a thumbnail viewing field 108 that may be used for displaying color ultrasound images, color MRI uptake curve or map images; or digitally captured paper reports.

Figure 2:
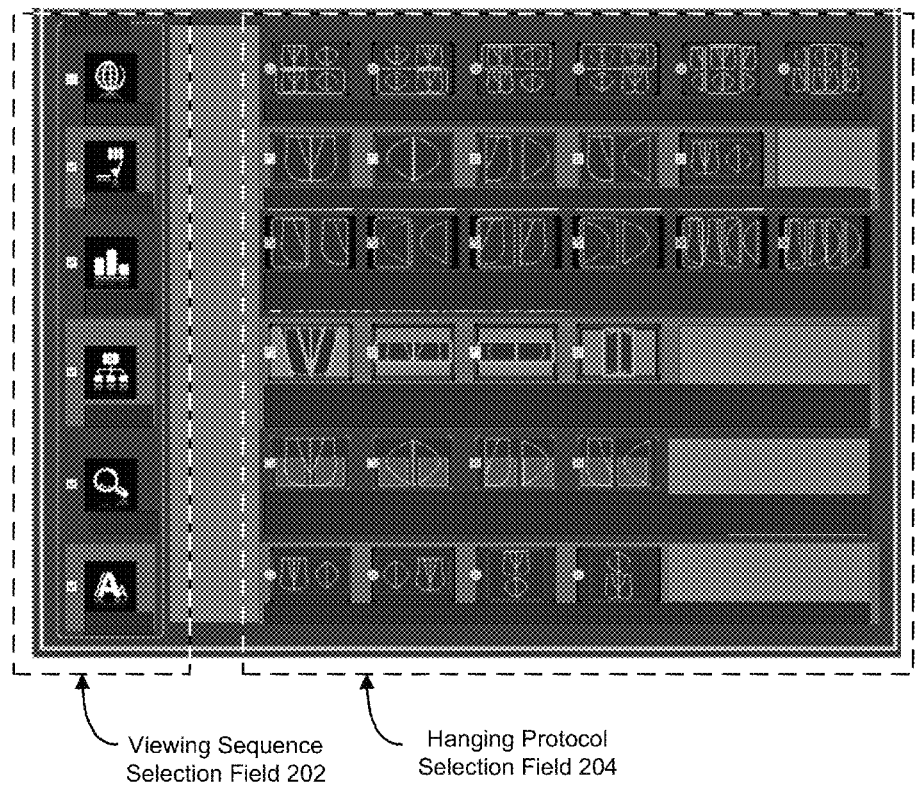
FIG. 2 depicts a viewing sequence configuration interface allowing a user to create a stepped viewing sequence for a mammographic case.

FIG. 2 depicts a viewing sequence configuration interface 200. The interface may allow a user to create a desired sequence for viewing or "reading" the images in a mammographic case. Viewing sequence configuration interface 200 may include a viewing sequence selection field 202 and a hanging protocol selection field 204. Viewing sequence configuration interface 200 may include a plurality of selectable buttons in both viewing sequence selection field 202 and hanging protocol selection field 204.

Viewing sequence selection field 202 may include a plurality of viewing options selectable by corresponding buttons. These buttons may include an overall viewing button, an image quality assessment button, a current-prior comparison button, a systematic perception viewing button, a full resolution viewing button, and a review and report button.

Selecting the overall viewing button may provide for overall viewing of standard four-view mammograms, which each include eight total images. These eight images may include a left and a right mediolateral oblique view and a left and a right craniocaudal view. These four images may be included from a current and a prior exam. Thus, eight images may be included. This option may provide an overall viewing for radiologists to make breast composition estimations. This may be performed according to Breast Imaging-Reporting and Data System (BIRADS®) breast density guidelines. Overall viewing of current and prior images may also enhance the detection of tissue density changes and overall viewing of the craniocaudal (CC) and mediolateral oblique (MLO) alternative views may enhance the detection on both view projections. Hanging protocol selection field 204 may include a plurality of associated buttons to allow a user to select a desired hanging protocol for use in overall viewing.

Selecting the image quality assessment button may include an image quality assessment step in the viewing sequence. The workstation may provide bilateral or unilateral two-view hanging protocols and a check list for quality assurance. The check list items may be entered by the user. The check list items may include checking whether any images are missing, whether the images are properly positioned with adequate breast compression, whether the images are of sufficient quality to make a diagnosis, and whether the images are correctly labeled. Hanging protocol selection field 204 may include a plurality of buttons corresponding to image views that may be included to allow a user to assess the quality of the images. The user may select a plurality of such views.

Selecting the current-prior comparison button may include same view breast comparisons between current exam and prior exam in the viewing sequence. These comparison views may enhance the detection of tissue density changes and calcification appearance or disappearance on the same view. The comparison views may include a single, standard mammography view, such as a current right MLO view image and a prior right MLO view image together. Additionally, the comparison views may include two standard-mammogram views. For example, a comparison view may include a current and a prior right MLO view and a current and a prior right CC view. A number of alternative views may be selectable by a user choosing among a plurality of buttons corresponding to the alternative views included in the hanging protocol selection field 204.

Figure 5A:
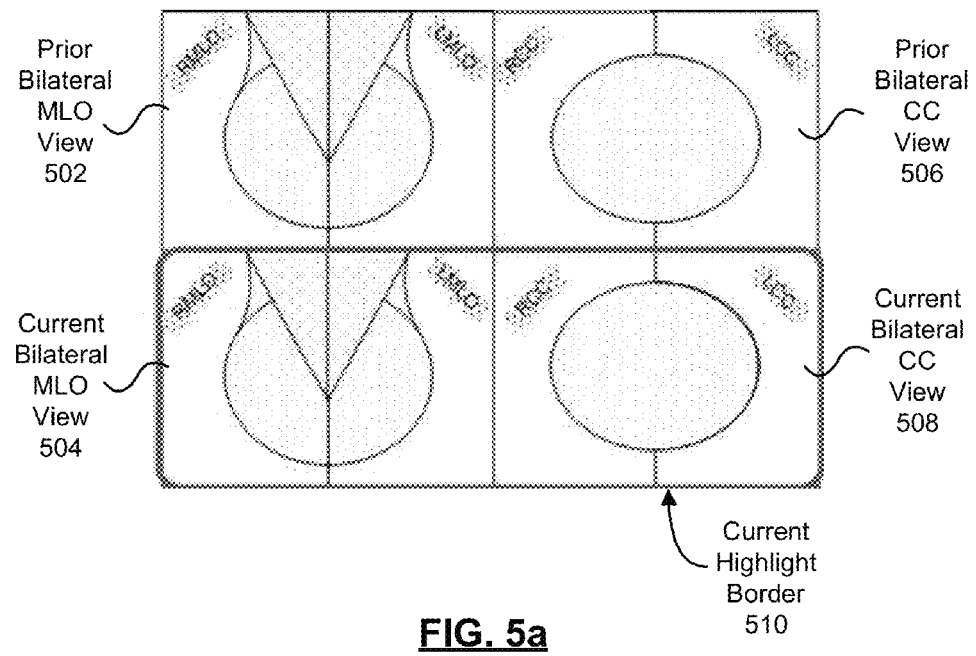
FIG. 5a depicts a 4-view mammography hanging protocol feature a highlighted border around current mammography views.
Figure 5B:
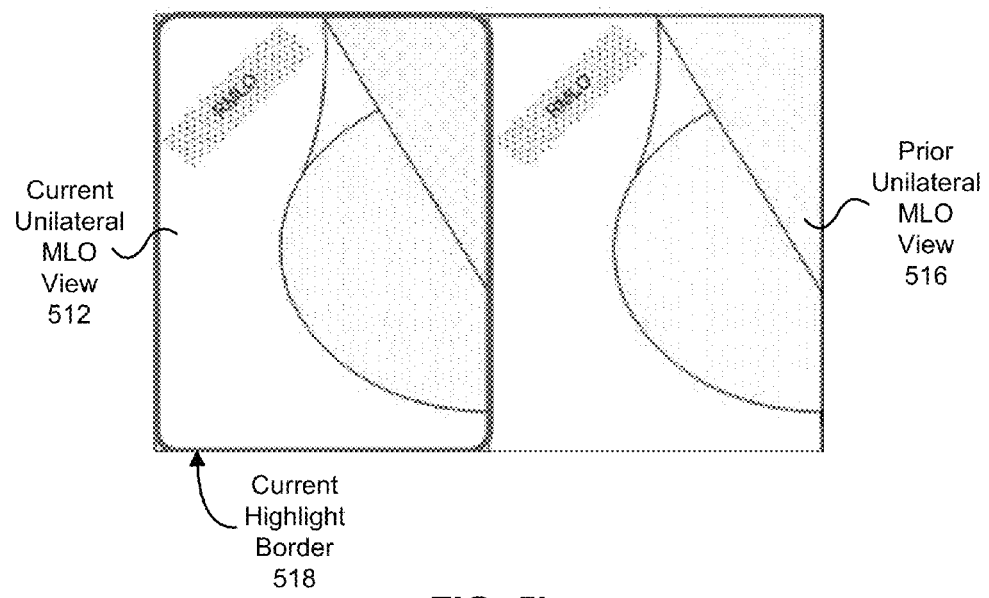
FIG. 5b depicts a current and prior mammography view with a highlighted border around current mammography view.

Exemplary current-prior comparison views are included in FIGS. 5a-b. FIG. 5a portrays a four-view (right and left MLO, and right and left CC) hanging protocol. Each view is bilateral, including a current image and a previously obtained image. Thus, FIG. 5a includes a prior bilateral MLO view 502, a current bilateral MLO view 504, a prior bilateral CC view 506, and a current bilateral CC view 508. The workstation may be configured to place a current highlight border 510 around the current images to aid the user in examining the images in their proper chronological context. In order to minimize the risk of misdiagnosis from prior exam, all the current images may be highlighted with a frame or border. This may apply to all hanging protocols. Additionally, some of the diagnosis tools, such as markups made by the user for later recall and reference, may be designed to be disabled to ensure that the diagnosis is made over the current exam.

Figure 7A:
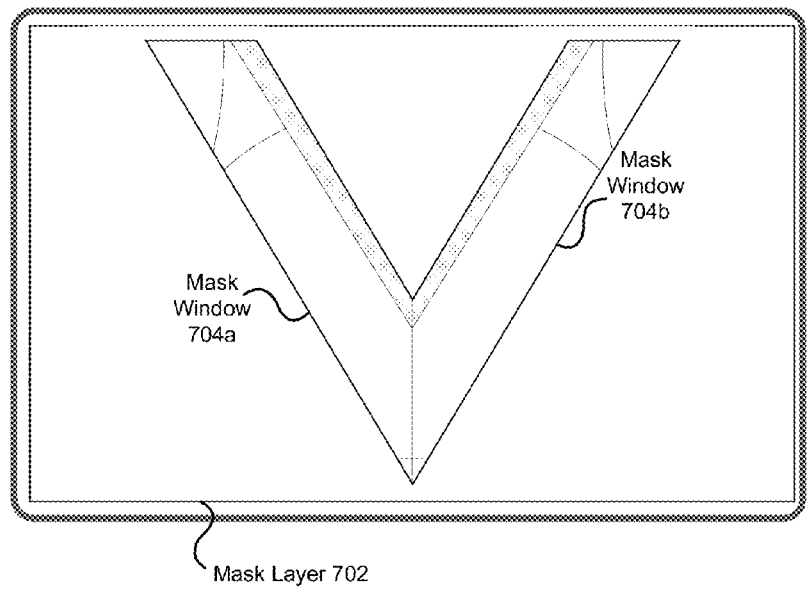
FIG. 7a depicts exemplary viewing masks over a bilateral mediolateral oblique mammogram image.
Figure 7A:
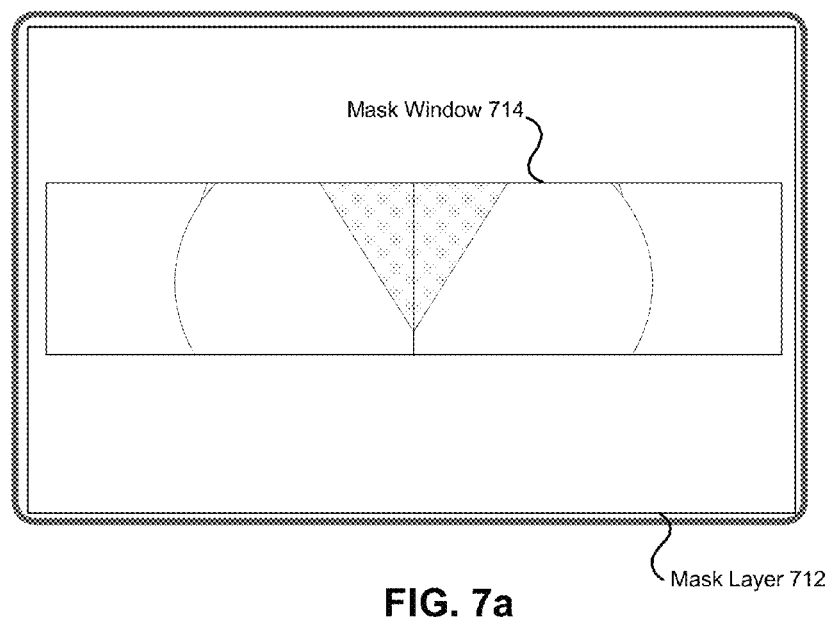
Figure 7B:
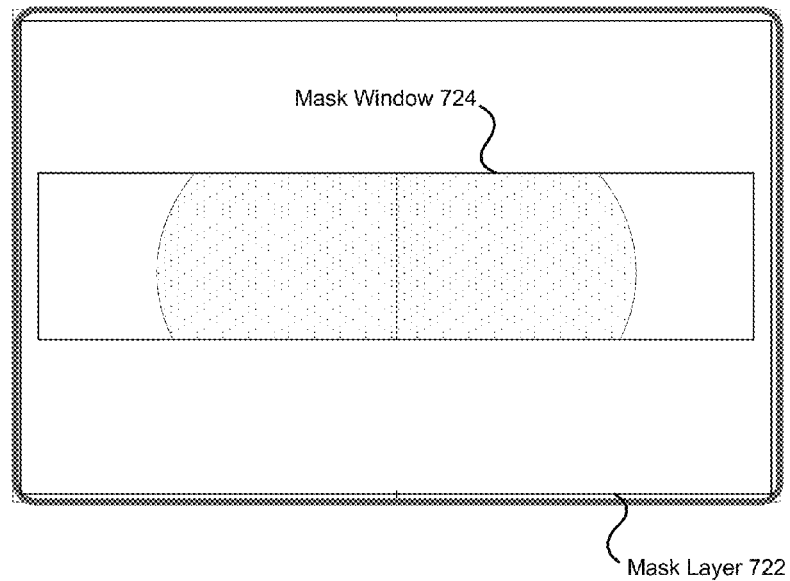
FIG. 7b depicts additional exemplary viewing masks over a bilateral mediolateral oblique mammogram image.
Figure 7B:
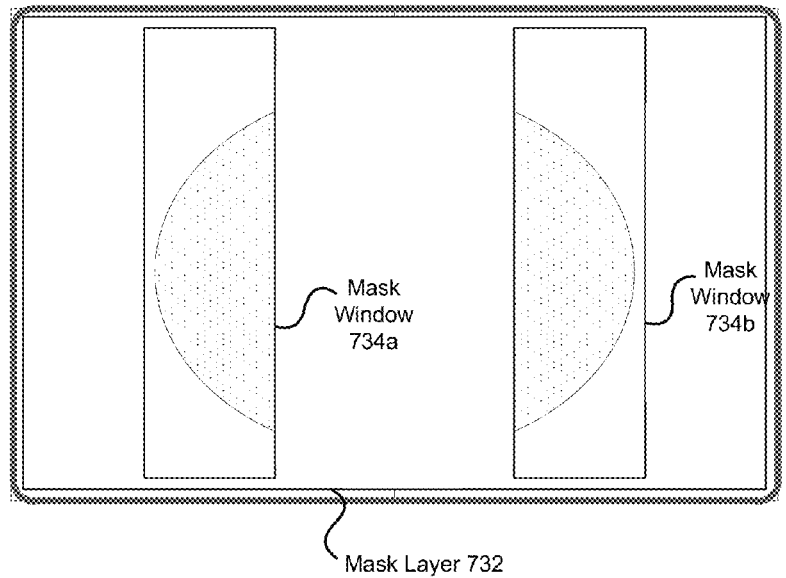

Selecting the systematic perception viewing button may include systematic perception viewing in the viewing sequence. This systematic perception viewing is based on an expert viewing methodology that has been used for viewing films and may be understood more easily with reference FIGS. 7a-b. The idea of systematic perception viewing is to use two types of masks to enhance perception of subtle radiographic abnormalities. FIGS. 7a-b depict four exemplary viewing masks 700a-d. Each viewing mask includes a mask layer and at least one mask window. The workstation may operate to provide for the mask layer, such as mask layers 702, 712, 722, and 732, by visually obscuring the underlying image except in mask window portions, such as mask windows 704a-b, 714, 724, and 734a-b.

A horizontal mask window, such as mask window 724 or 714 may be moved craniocaudally step-by-step, either on a bilateral MLO views or the bilateral CC views. An angled mask window, such as mask windows 704a or 704b, or a vertical mask window, such as mask window 734a or 734b, may be moved away from the pectoral muscle or chest wall step-by-step on the bilateral MLO views or CC views. By use of the masks, special attention can be given to asymmetric densities in regions with a high probability of malignant lesions. The systematic perception viewing method may enable the user-radiologist to differentiate with increased confidence between the normal and the abnormal tissue by accounting for the radiopaque structure components that are seen against the radiolucent background.

A plurality of viewing mask buttons may be provided in hanging protocol selection field 204. Each of the viewing mask buttons may include a different bilateral image with an appropriate viewing mask into the viewing sequence. A user may select one or more systematic viewing images for inclusion in the viewing sequence. The workstation may enable a user to control the movement or position of the mask windows at user defined step intervals. The user may further be able to control the opacity of the mask layer, the color and thickness of a border which may surround the mask window, and the size and angle of the mask window.

Selecting the full resolution view button may include a full-resolution "all pixel" image view or views into the viewing sequence. In many available monitors or computer displays, only a portion of an image can be displayed at one time at full resolution, because the image may include more pixels than the monitor. Manually panning and zooming on the computer monitor, while possible, is not natural for radiologists. It can be inefficient and it may be physically tiring and time-consuming. The full-resolution viewing may be better understood with reference to FIGS. 8a-b. The provided method 800 for full-resolution image viewing may allow for more efficient searching through all pixels in an image in such a way that a user may navigate an entire image at full resolution using an input device as simple as a mouse scroll-wheel.

Figure 8A:
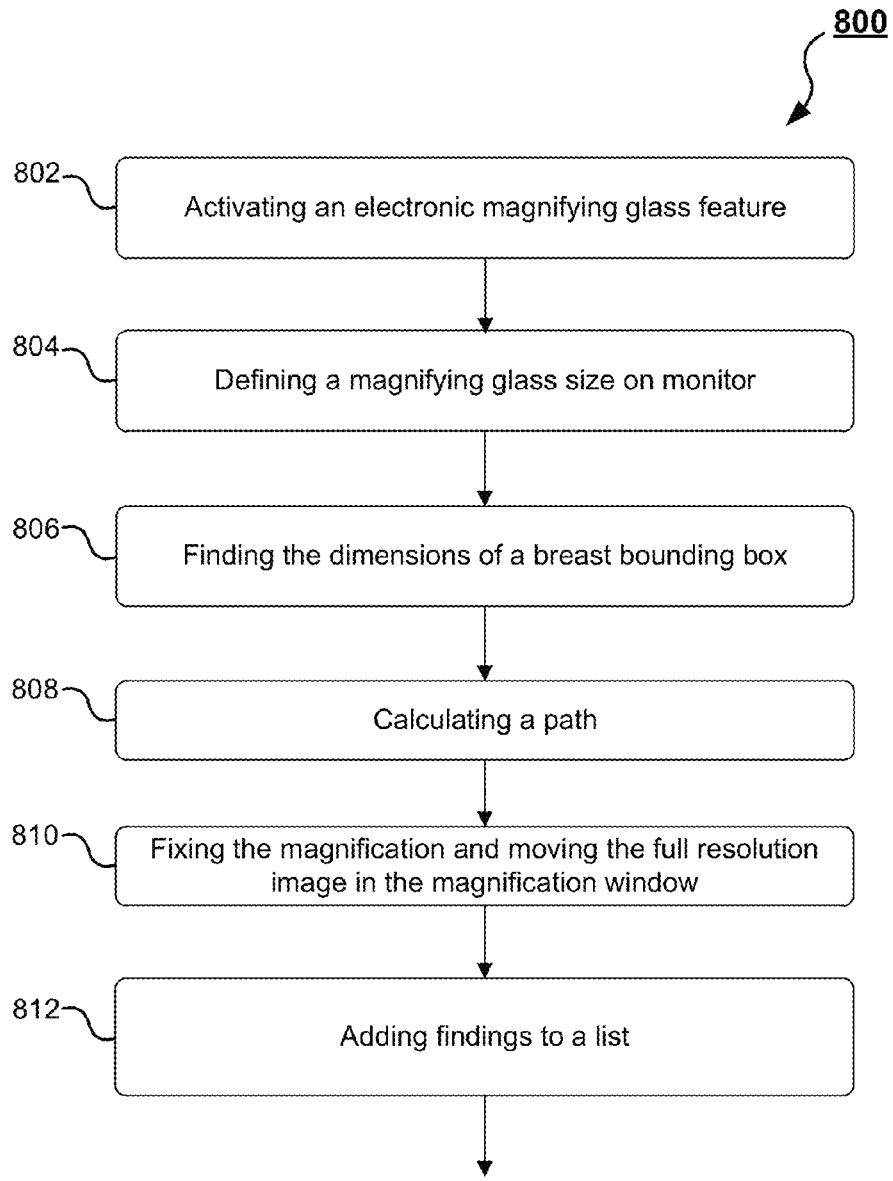
FIG. 8a is a flowchart of a method for providing mouse wheel navigation of an image at full resolution, when the image is larger than the display.

In FIG. 8a, method 800 may begin in step 802 when a user activates an electronic magnifying glass feature. This may be done automatically when a user has selected the full resolution button in the viewing sequence selection field 202 while configuring a desired viewing sequence. The electronic magnifying glass feature may be activated when the user reaches an image that is to be displayed in full resolution viewing.

The electronic magnifying glass may be a window in the foreground of an image that displays a portion of the image in the background but at a higher resolution. The size (M×M) of the magnifying glass may be defined in step 804. The dimensions (Bx, By) of a breast bounding box may be found in step 806. In step 808, the workstation application may automatically calculate a path by which the user may step through the full resolution image a full-resolution portion at a time. The workstation application may calculate a number of vertical path steps as (Bx/M)/2−1. A number of horizontal path steps may be calculated as equal to (By/M)/2−1. This may allow for a 50% overlap in the steps. In step 810, the magnification may be fixed and the user may move the full resolution image in the magnification window. The user may make findings on the full resolution portion and add the findings to a list in step 812.

Figure 8B:
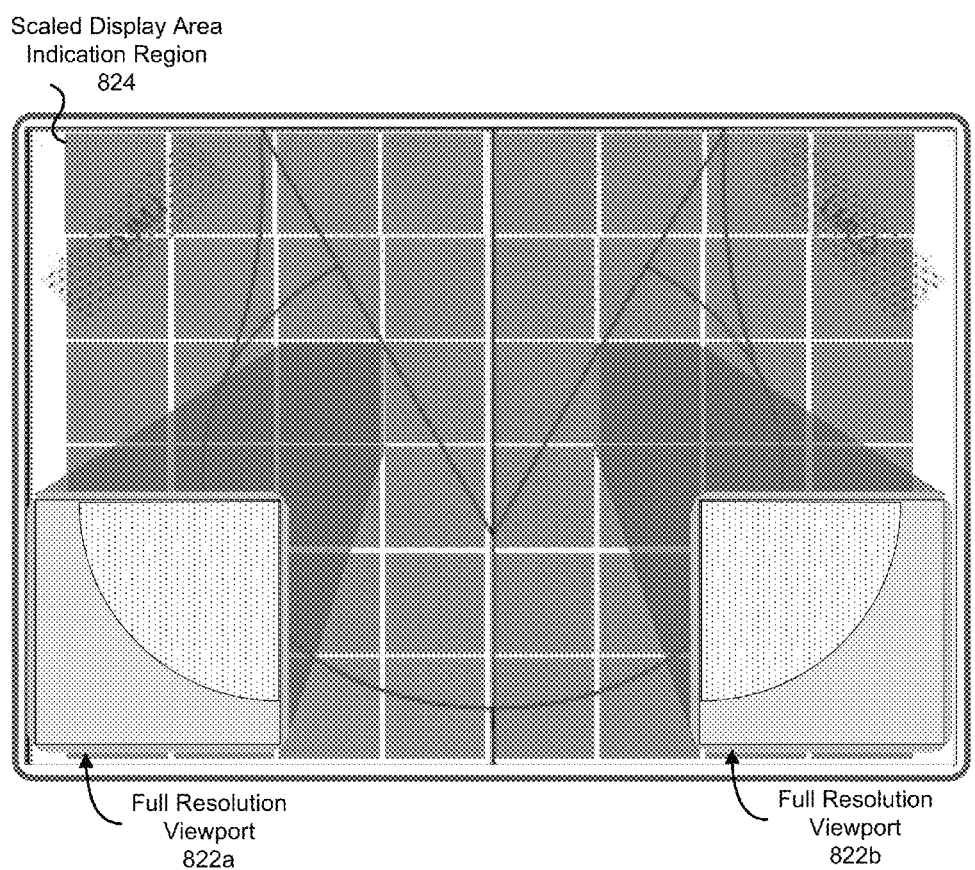
FIG. 8b depicts an exemplary view of a scaled image viewed portion by portion at full resolution in an overlaid window.

FIG. 8b schematically depicts what a user may see when using the full resolution viewing method 800. The image to be viewed, which may be unilateral or bilateral, is scaled to fit in the background. The image is visibly subdivided into scaled display area indication regions, such as scaled display area indication region 824, that will be displayed in a full resolution window, such as full resolution display area 822a or 822b when selected by the user. Visual feedback may be provided to a user using a transparent or translucent graphic to indicate which portions of the scaled image have been displayed in the full resolution display area or areas. The user may move through the divided portions, by using the scroll-wheel on a mouse or other input device, the portion displayed at full resolution may be determined by the position on the automatically calculated path. Once all of the image portions have been viewed in the full resolution display area, the workstation application may then provide a visual indication.

Figure 9:
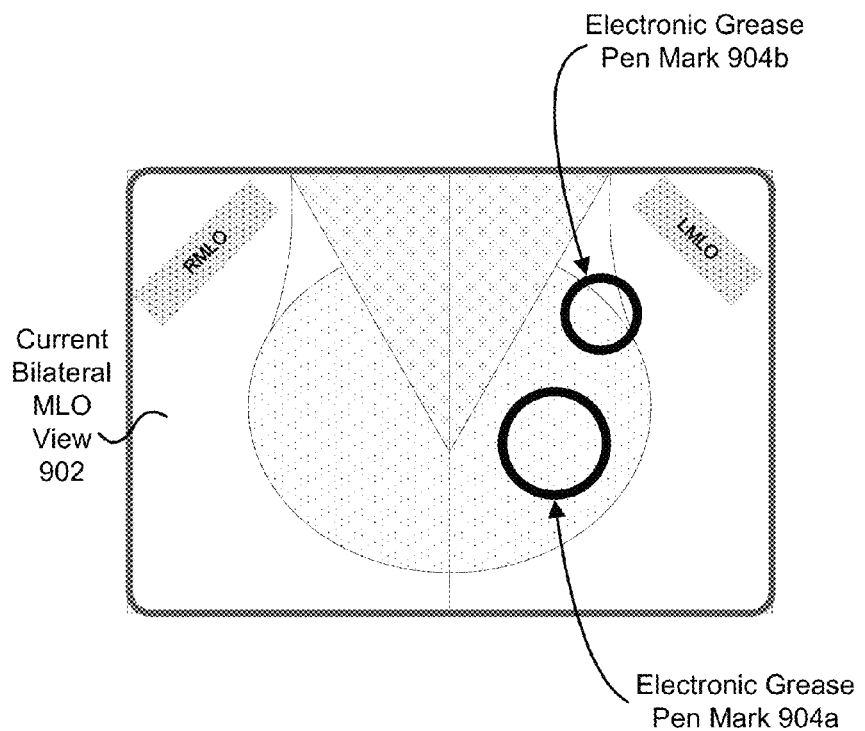
FIG. 9 depicts an exemplary bilateral mammogram image with electronic grease pen marks.
Figure 10:
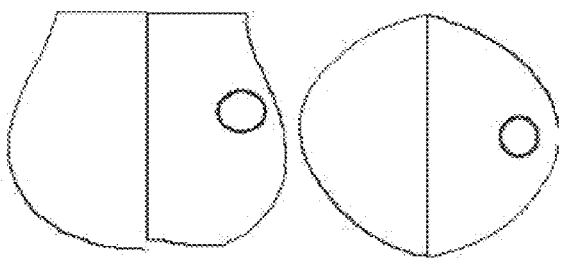
FIG. 10 depicts an exemplary, automatically generated report.

Selecting the review and report button may provide an end to the viewing sequence selected through the viewing sequence configuration interface 200. The review and report button may allow the user to review findings made throughout the preceding portion of the viewing sequence and to automatically generate a report based on those findings. Generating the reports may include providing a user interface to markup lesion findings using an electronic grease pen, as shown in FIG. 9, and facilitating screen captures of the markups and images for inclusion in the report as seen in FIG. 10. The report may include the location of the lesion markup, the type of the lesion markup, markup assessments, and the recall procedures.

FIG. 9 depicts the use of an electronic grease pen. The workstation may provide an "electronic grease pen" to allow the user to make marks on the image displayed in any hanging protocol in any viewing step, as might be done if the user were viewing the images in film form. FIG. 9 depicts a current bilateral MLO view image 902. FIG. 9 also includes two exemplary electronic grease pen marks 904a and 904b. The marks may be considered by the user as initial findings and can be removed by user. The display of the electronic markup can be toggled on and off. The electronic grease pen marks 904a-b may be automatically captured and associated position information may be automatically reflected in the report.

FIG. 10 depicts an exemplary report 1000. Such a report may be automatically created if the review and report button has been selected for inclusion in the viewing sequence.

Returning attention to FIG. 2, the user may use viewing sequence selection field 202 and hanging protocol selection field 204 in viewing sequence configuration interface to create a viewing sequence by inclusion or exclusion, selection or non-selection of the options presented. Visual sequence configuration interface 202 may allow the user to define his or her viewing step in the viewing sequence and the corresponding hanging protocols for each step. For all hanging protocols defined in the configuration tool, the workstation may automatically perform the chest wall and/or tissue or muscle alignment using a breast mask bounding box.

Figure 3A:
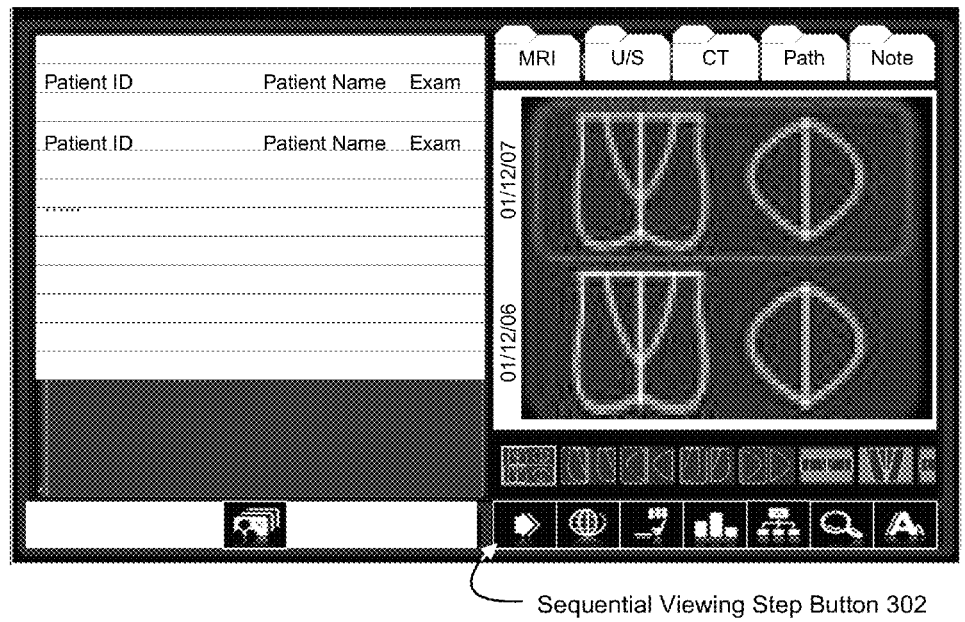
FIG. 3a depicts a sequential viewing step button in a navigation interface.
Figure 3B:
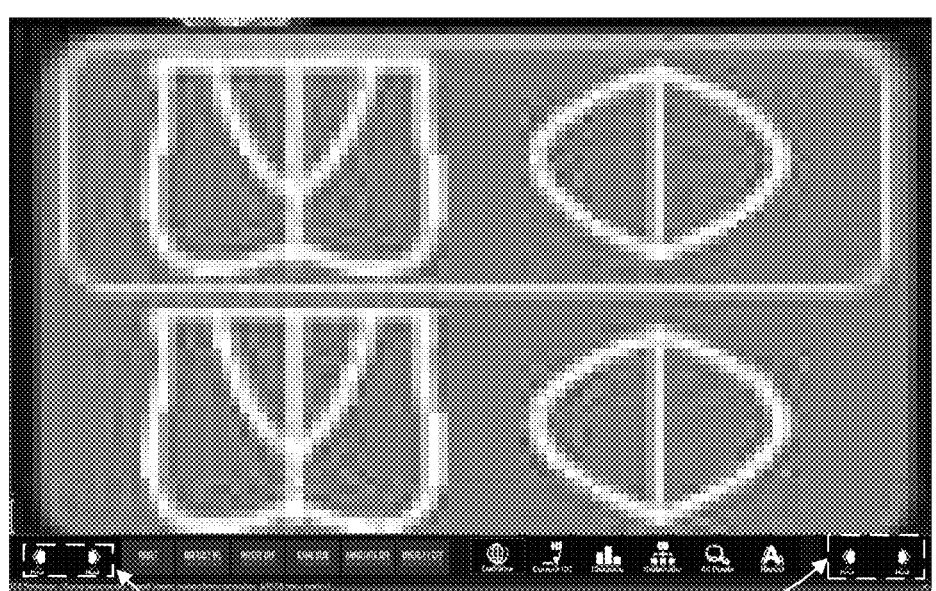
FIG. 3b depicts two sets of sequential viewing step buttons in a full screen view.

FIG. 3a depicts navigation interface 100 as seen also in FIG. 1. Navigation interface 100 may provide for viewing of the viewing sequence created by the user in the thumbnail viewing field 102. The user may step through the viewing sequence or workflow one hanging protocol at a time by repeatedly clicking a sequential viewing step button 302. Additionally, the viewing sequence may also be viewed in an image interface 300 as depicted in FIG. 3b. The image interface 300 of FIG. 3b may allow for full screen viewing of each hanging protocol in the sequence. Image interface 300 may be used to display high-resolution gray-scale mammogram images and associated overlays for the purpose of primary interpretation by users. Image interface 300 may include sequential viewing step buttons 304. Sequential viewing step buttons 304 may include a next step button and a previous step button. These buttons may allow a user to step forward or backward in the selected viewing sequence or workflow. Additionally a user may use the right arrow key, to progress through all the configured viewing steps and all the configured hanging protocols.

Generally, any operation that might be used within each hanging protocol and viewing step can be performed by clicking the up or down button or equivalently using the arrow key or mouse wheel. For example, in the step of systematic perception viewing, the mouse wheel may move the mask up or down. Or in the step of full-resolution all pixel viewing, the mouse wheel may move the trace of viewing window up or down.

Figure 4:
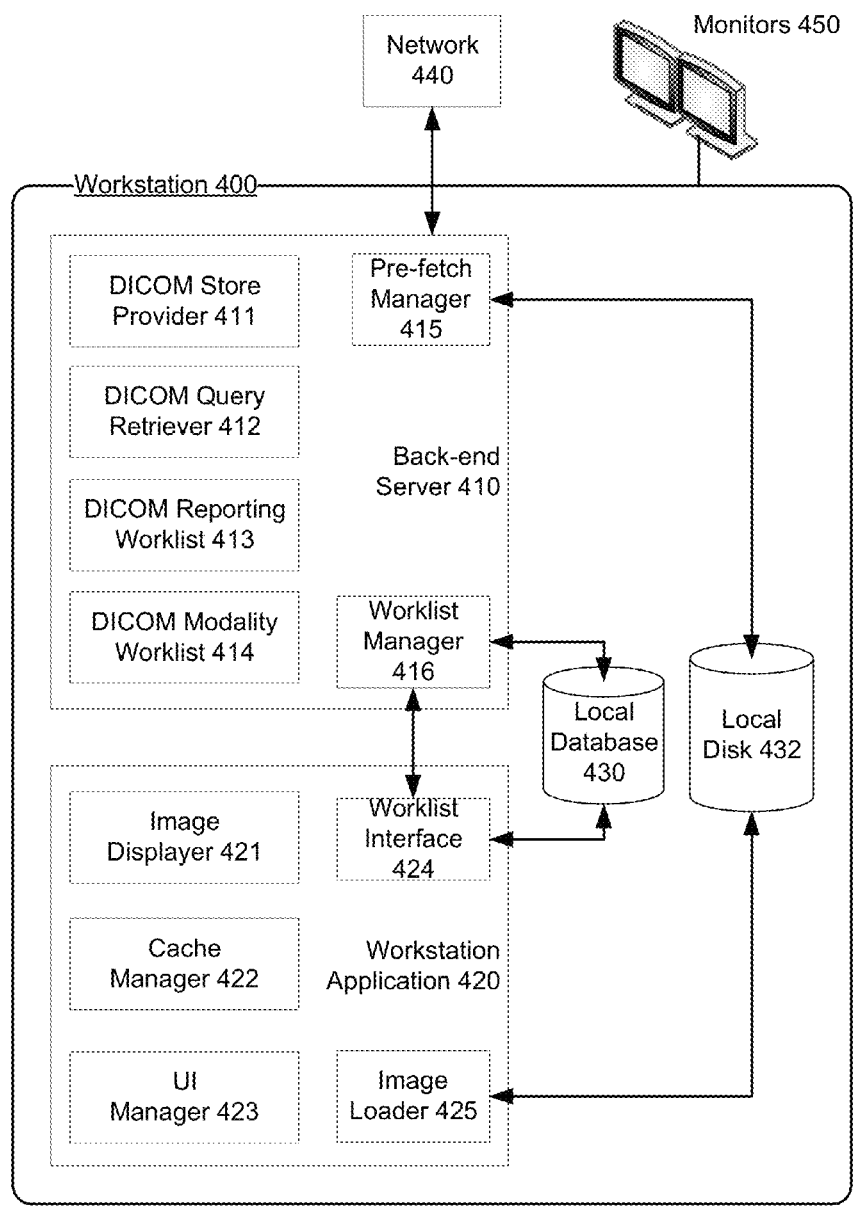
FIG. 4 depicts a mammography workstation capable of providing the stepped viewing sequence.

FIG. 4 depicts a workstation 400 that may be used to provide navigation interface 100, viewing sequence configuration interface 200, the image screen of FIG. 3b, and the numerous features described above. As depicted in FIG. 4, workstation 400 may include a back-end server 410 to communicate with a remote DICOM service available on network 440. Back-end server 410 may include a DICOM store provider 411, a DICOM query retriever 412, a DICOM reporting worklist 413, a DICOM modality worklist 414, a pre-fetch manager 415, and a worklist manager 416. Workstation 400 may also include a workstation application 420. Workstation 420 may include an image displayer 421, a cache manager 422, a user interface (UI) manager 423, a worklist interface 424 and an image loaded 425. Additionally, workstation 400 may include a local database 430, which may be stored on a local disk 432. Workstation 400 may display visuals on monitors 450. As mentioned above, workstation 400 may also include a computer processor (not depicted).

These numerous features may allow workstation 400 to implement the two-level on-demand pre-fetching/caching mechanisms described above and further operations customarily performed by radiographic imaging workstations. Ensuring that image data is available on the monitor or monitors almost immediately may optimize the performance seen by the user once the user opens next case. In order to achieve this impression, the workstation 400 may incorporate so-called two-level on-demand pre-fetching/caching mechanisms.

The first level of the on-demand method may ensure that the data resides on the workstation prior to the initiation of the display. This may be referred to as "pre-fetching" the images. While it can be imagined that images can be retrieved rapidly on demand from an archive, some existing systems and certainly sites with high workloads on their networks may not see usable interactive speed without pre-fetching. Thus the architecture of the workstation will explicitly include pre-fetching and utilizing a "reading worklist" such as case worklist 106 of FIG. 1 to order the cases for retrieval. The second level of the on-demand method may ensure that the data is in the computer memory once the user navigates to a case by providing an explicit mechanism to make the next available case resident in system memory prior to the user navigating to that case. The mechanism to get a case into memory prior to its display is here referred to as "caching".

Figure 6:
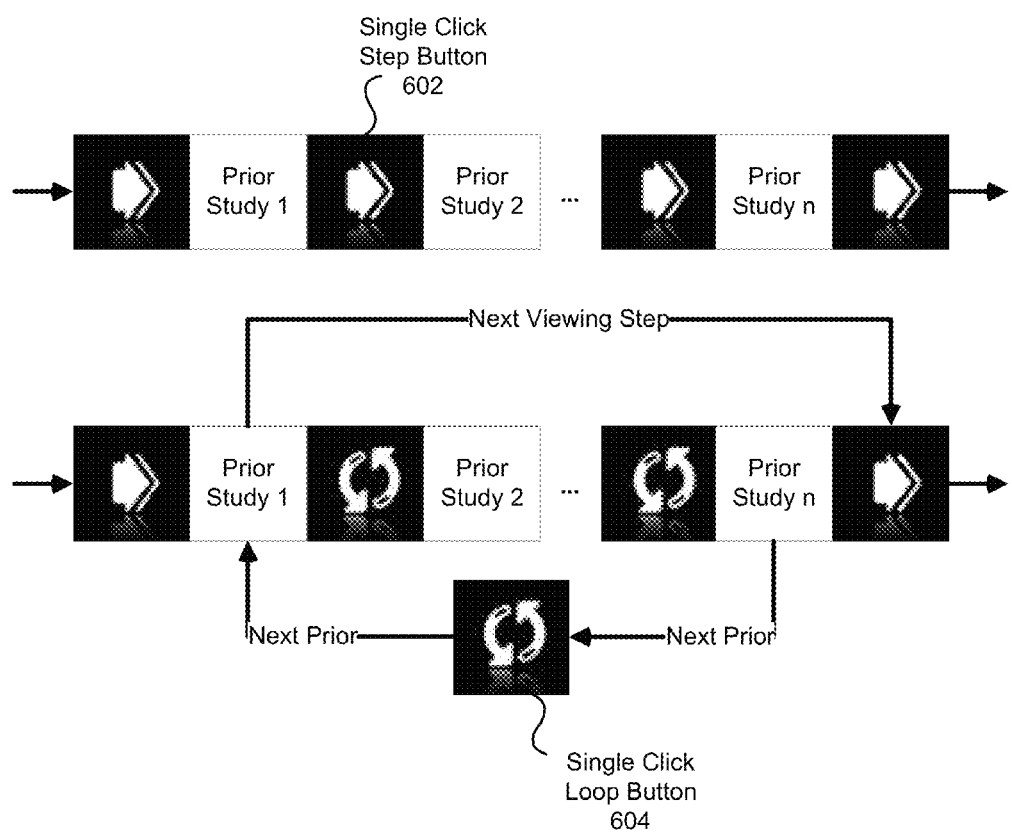
FIG. 6 depicts a single click button used to step through multiple prior exams.

FIG. 6 depicts a stepping button, single click step button 602, that may be used to step through each prior exam. The system can also be configured so a separate looping button, single click loop button 604, can be used to step through each prior study.

The invention claimed is:

1. A mammography workstation comprising:
   at least one computer display;
   a computer processor connected to the at least one computer display, the computer processor also connected to a local memory storage device and a Digital Imaging and Communications in Medicine (DICOM) service;
   a workstation application running on the computer processor, the workstation application configured to provide a user interface to be displayed on the at least one computer display, the user interface comprising a viewing sequence configuration interface that includes a plurality of selectable buttons, the selection of which results in a stepped viewing sequence of mammogram images arranged in hanging protocols, the stepped viewing sequence including at least one standard 4-view mammogram, at least one 2-view mammogram, at least one comparison view, and a bilateral mammogram image with an overlaid viewing mask; and
   at least one input device suitable to allow a user to select desired buttons of the plurality of selectable buttons and to allow a user to step through the stepped viewing sequence of mammogram images according to the stepped viewing sequence created using the viewing sequence configuration interface.

2. The workstation of claim 1, wherein the at least one input device comprises a computer mouse with a scrolling mechanism and/or a computer keyboard.

3. The workstation of claim 2, wherein the viewing sequencing configuration interface comprises:
   a viewing sequence step selection field, the viewing sequence step selection field including a plurality of selectable viewing step buttons; and
   a hanging protocol selection field, the hanging protocol selection field including a plurality of mammogram image buttons, each of the plurality of mammogram image buttons displaying an associated one of a plurality of mammogram images, each of the plurality of mammogram images being arranged in a hanging protocol.

4. The workstation of claim 3, wherein the plurality of selectable viewing step buttons comprises:
   an overall viewing step button, the selection by the user of the overall viewing step button causing the at least one standard 4-view mammogram to be included in the stepped viewing sequence;
   an image quality assessment button, the selection by the user of the image quality assessment button causing the at least one 2-view mammogram and a quality assurance check list to be included in the stepped viewing sequence;
   a current-prior comparison button, the selection by the user of the current-prior comparison button causing the at least one comparison view to be included in the stepped viewing sequence, the comparison view presenting a current mammogram and a corresponding prior mammogram simultaneously;
   a systematic perception view button, the selection by the user of the systematic perception view button causing the bilateral mammogram image with an overlaid viewing mask to be included in the stepped viewing sequence;
   a full resolution view button, the selection by the user of the full resolution view button causing a display of a portion of at least one mammogram in which one pixel of the mammogram is displayed by one pixel on the at least one computer display to be included in the stepped viewing sequence; and
   a review and report button, the selection by the user of the review and report button enabling a user to mark areas of diagnostic concern on those images of the plurality of mammogram images that are selection for inclusion in the stepped viewing sequence, the user enable to mark those images with the at least one input device and causing the areas of diagnostic concern to be included in an automatically generated report created at the end of the viewing sequence.

5. The workstation of claim 4, wherein the plurality of mammogram image buttons comprises:
   a plurality of standard 4-view mammogram image buttons;
   a plurality of 2-view mammogram image buttons;
   a plurality of comparison view buttons;
   a plurality of bilateral view buttons, each of the plurality of bilateral view buttons including a viewing mask;
   a plurality of full resolution buttons; and
   a plurality of matched view buttons, each of the matched view buttons including a bilateral craniocaudal mammogram and a bilateral mediolateral oblique mammogram.

6. The workstation of claim 5, wherein each of the plurality of mammogram image buttons comprises a thumbnail view of a corresponding mammogram image associated with each mammogram image button, the selection of any of the plurality of mammogram image buttons causing the corresponding image to be included in the stepped viewing sequence.

7. The workstation of claim 6, wherein the computer processor generates the stepped viewing sequence of mammogram images after the user has completed selections using the viewing sequence configuration interface.

8. The workstation of claim 4, further comprising:
   a pre-fetch manager, the pre-fetch manager accessing the DICOM service to retrieve the plurality of mammogram images and storing the plurality of mammogram images on the local memory storage device; and
   a cache manager, the cache manager configured to place the plurality of mammogram images or a subset thereof on a computer cache connected to the computer processor.

9. The workstation of claim 8, wherein:
   the workstation application is configured to provide a workflow navigation interface, the workflow navigation interface comprising a list of cases to be reviewed by the user;

the pre-fetch manager is configured to access, retrieve, and locally store a next plurality of mammogram images through the DICOM service, the next plurality of mammogram images being associated with a next case on the list of cases that has not been reviewed and is not being reviewed currently by the user; and the cache manager is configured to place the next plurality of mammogram images on the computer cache before the next case is reviewed by the user.

10. The workstation of claim 1, wherein the viewing mask to be presented over a bilateral mammogram image comprises:

a mask layer, the mask layer being superimposed over the bilateral mammogram image and visually obscuring the bilateral mammogram image; and a viewing mask window, the viewing mask window being a parallelogram that causes an area contained by the parallelogram to appear unobscured by the mask layer.

11. The workstation of claim 10, wherein the parallelogram of the viewing mask window is definable by the user in terms of an angle of orientation, geometric dimensions, and in terms of position relative to the bilateral mammogram image visually underlying the mask layer.

12. The workstation of claim 11, wherein the viewing mask window comprises an additional parallelogram if the angle of orientation defined by the user is not horizontal, the parallelogram and the additional parallelogram having corresponding geometric dimensions and being jointly positioned by the user relative to the bilateral mammogram image.

13. The workstation of claim 12, wherein the bilateral mammogram image comprises a right mediolateral oblique (MLO) view and a left MLO view, the parallelogram being superimposed over the right MLO view and the additional parallelogram is superimposed over the left MLO view.

14. The workstation of claim 13, wherein the parallelogram is aligned to the pectoral muscle in the right MLO view and the additional parallelogram is aligned to the pectoral muscle in the left MLO view.

15. The workstation of claim 14, wherein the parallelogram is moveable from the pectoral muscle in the right MLO view toward a nipple in the right MLO view and the additional parallelogram is moveable from the pectoral muscle in the left MLO view toward a nipple in the left MLO view.

* * * * *